US009833196B2

(12) United States Patent
Sarrafzadeh et al.

(10) Patent No.: US 9,833,196 B2
(45) Date of Patent: Dec. 5, 2017

(54) APPARATUS, SYSTEM, AND METHOD FOR DETECTING ACTIVITIES AND ANOMALIES IN TIME SERIES DATA

(75) Inventors: Majid Sarrafzadeh, Anaheim Hills, CA (US); Alireza Vahdatpour, Kirkland, WA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 559 days.

(21) Appl. No.: 14/002,661

(22) PCT Filed: Mar. 1, 2012

(86) PCT No.: PCT/US2012/027328
§ 371 (c)(1),
(2), (4) Date: Oct. 17, 2013

(87) PCT Pub. No.: WO2012/118998
PCT Pub. Date: Sep. 7, 2012

(65) Prior Publication Data
US 2014/0039274 A1 Feb. 6, 2014

Related U.S. Application Data

(60) Provisional application No. 61/448,602, filed on Mar. 2, 2011.

(51) Int. Cl.
*G01N 33/48* (2006.01)
*A61B 5/00* (2006.01)
*G06K 9/00* (2006.01)
*A61B 5/0402* (2006.01)
*A61B 5/0476* (2006.01)
*A61B 5/11* (2006.01)

(52) U.S. Cl.
CPC .............. *A61B 5/7271* (2013.01); *A61B 5/11* (2013.01); *A61B 5/1118* (2013.01); *A61B 5/6802* (2013.01); *A61B 5/7246* (2013.01); *A61B 5/7264* (2013.01); *A61B 5/746* (2013.01); *G06K 9/00536* (2013.01); *A61B 5/0402* (2013.01); *A61B 5/0476* (2013.01); *A61B 5/1112* (2013.01)

(58) Field of Classification Search
None
See application file for complete search history.

(56) References Cited

U.S. PATENT DOCUMENTS

| 2010/0302043 A1 | 12/2010 | Skubic et al. |
| 2010/0324456 A1 | 12/2010 | Jonsson et al. |
| 2011/0028856 A1 | 2/2011 | Zhang et al. |
| 2011/0112442 A1* | 5/2011 | Meger ............... A61B 5/0002 600/595 |

OTHER PUBLICATIONS

Vahdatpour A, Amini N, Sarrafzadeh M. "Toward Unsupervised Activity Discovery Using Multi-Dimensional Motif Detection in Time Series" (InIJCAI Jul. 11, 2009 vol. 9, pp. 1261-1266).*
Lan M, Nahapetian A, Vahdatpour A, Au L, Kaiser W, Sarrafzadeh M. SmartFall: an automatic fall detection system based on subsequence matching for the SmartCane. InProceedings of the Fourth International Conference on Body Area Networks Apr. 1, 2009 (p. 8). ICST (Institute for Computer Sciences, Social-Informatics and Telecommunications Engineering).*
International Search Report PCT/US2012/027328 dated Sep. 25, 2012.
Vahdatpour, et al., "Unsupervised Discovery of Abnormal Activity Occurrences in Multi-dimensional Time Series, with Applications in Wearable Systems", SIAM International Conference on data mining, pp. 641-652, (2010).

* cited by examiner

*Primary Examiner* — Anna Skibinsky
(74) *Attorney, Agent, or Firm* — Foley & Lardner LLP; Cliff Z. Liu (57) ABSTRACT

Activities and abnormalities in activities are detected by: (1) receiving data corresponding to measurements of an activity occurring during a time interval; (2) determining a plurality of primitives associated with the data, wherein each of the plurality of primitives represents a characteristic pattern in a portion of the time interval; (3) derive an activity structure relating a first subset of the plurality of primitives that are correlated in time; and (4) based on the activity structure, classify a second subset of the plurality of primitives as an abnormal instance of the bodily activity.

20 Claims, 4 Drawing Sheets

APPARATUS, SYSTEM, AND METHOD FOR DETECTING ACTIVITIES AND ANOMALIES IN TIME SERIES DATA

CROSS-REFERENCE TO RELATED APPLICATION

This application is a National Stage Entry of PCT/US2012/027328 filed on Mar. 1, 2012, which claims the benefit of U.S. Provisional Application Ser. No. 61/448,602 filed on Mar. 2, 2011, the disclosure of which is incorporated herein by reference in its entirety.

FIELD OF THE INVENTION

The invention generally relates to the detection of activities and abnormalities and, more particularly, to the detection of activities and anomalies in time series data.

BACKGROUND

Techniques of detecting anomalies in time series data have been studied in recent years. The main purpose of anomaly detection in time series is to locate events and time instances where irregular actions or patterns occur. Depending on the specifications of different applications, several definitions for anomaly have been proposed. For example, discord in time series can include subsequences (with a predefined length) that are maximally different to all of the rest of the time series subsequences. A symbolic aggregate approximation (SAX) technique has been used to locate such subsequences. As another example, an anomaly can be considered as a sufficiently infrequent time series pattern. A pattern can be considered to be sufficiently infrequent or surprising if the frequency of its occurrences differs substantially from what is expected according to previous experience. Linear characteristics of suffix trees have been used to extract such patterns from long time series.

Despite the progress made to date, current techniques of anomaly detection suffer from certain deficiencies. In particular, current techniques typically rely upon a priori information about time sequences in order to detect anomalies. Also, the deficiency of current techniques has been reported when such techniques are applied to time series data collected from wearable sensors.

It is against this background that a need arose to develop the apparatus, system, and method described herein.

SUMMARY

One aspect of the invention relates to a non-transitory computer-readable storage medium. In one embodiment, the storage medium includes executable instructions to: (1) receive data corresponding to measurements of a bodily activity occurring during a time interval; (2) determine a plurality of primitives associated with the data, wherein each of the plurality of primitives represents a characteristic pattern in a portion of the time interval; (3) derive an activity structure relating a first subset of the plurality of primitives that are correlated in time; and (4) based on the activity structure, classify a second subset of the plurality of primitives as an abnormal instance of the bodily activity.

In another embodiment, the storage medium includes executable instructions to: (1) receive time series data corresponding to sensor measurements including components in a plurality of dimensions; (2) determine a plurality of subsequences associated with the time series data, wherein each of the plurality of subsequences represents a characteristic pattern projected along one of the plurality of dimensions; (3) identify a first subset of the plurality of subsequences as a normal instance of a first bodily activity based on a degree of temporal overlap of members of the first subset; (4) identify a second subset of the plurality of subsequences as an abnormal instance of the first bodily activity based on comparing the second subset to the first subset; and (5) generate an indication of the abnormal instance of the first bodily activity.

In another embodiment, the storage medium includes executable instructions to: (1) receive discrete event data about a bodily activity occurring during a time interval; (2) determine a plurality of events associated with the data, wherein each of the plurality of events represents a characteristic pattern in a portion of the time interval; (3) derive an activity structure relating a first subset of the plurality of events that are correlated in time; and (4) based on the activity structure, classify a second subset of the plurality of events as an abnormal instance of the bodily activity.

In another embodiment, the storage medium includes executable instructions to: (1) receive a combination of multi-dimensional time series and discrete event data about a bodily activity occurring during a time interval; (2) determine a plurality of primitives and events associated with the time series and the data, wherein each of the plurality of primitives and events represents a characteristic pattern in a portion of the time interval; (3) derive an activity structure relating a first subset of the plurality of primitives and events that are correlated in time; and (4) based on the activity structure, classify a second subset of the plurality of primitives and events as an abnormal instance of the bodily activity.

In another embodiment, the storage medium includes executable instructions to: (1) receive a combination of location data, multi-dimensional time series, and discrete event data about a bodily activity occurring during a time interval; (2) determine a plurality of locations, primitives, and events associated with the location data, multi-dimensional time series, and discrete event data, wherein each of the plurality of locations, primitives, and events represents a characteristic pattern in a portion of the time interval; (3) derive an activity structure relating a first subset of the plurality of locations, primitives, and events that are correlated in time; and (4) based on the activity structure, classify a second subset of the plurality of locations, primitives, and events as an abnormal instance of the bodily activity.

Another aspect of the invention relates to a system for abnormality detection. In one embodiment, the system includes: (1) a processing unit; and (2) a memory connected to the processing unit and including executable instructions to: (a) receive an identification of a first multi-dimensional subsequence in a multi-dimensional time series as a normal instance of a bodily activity, wherein the multi-dimensional time series correspond to sensor measurements of the bodily activity; and (b) identify a second multi-dimensional subsequence in the multi-dimensional time series as an abnormal instance of the bodily activity based on a degree of similarity between members of the second multi-dimensional subsequence and members of the first multi-dimensional subsequence.

Other aspects and embodiments of the invention are also contemplated. The foregoing summary and the following detailed description are not meant to restrict the invention to any particular embodiment but are merely meant to describe some embodiments of the invention.

BRIEF DESCRIPTION OF THE DRAWINGS

For a better understanding of the nature and objects of some embodiments of the invention, reference should be made to the following detailed description taken in conjunction with the accompanying drawings.

DETAILED DESCRIPTION

In some embodiments, an apparatus, system, and method to detect anomalies (or abnormalities) in time series data are disclosed. In some embodiments, this data is multi-dimensional data that is typically captured or collected from several sources (e.g., several wearable sensors on the human body). Alternatively, or in combination, the time series data can be single-dimensional. Alternatively, or in combination with the time series data, other types of data can be processed, such as location data (e.g., Global Positioning System (GPS) data), discrete event data (e.g., questionnaire data, user feedback, or other data collected from discrete resources), or both. In some embodiments, a normal structure of the data is determined via an unsupervised activity discovery technique. The unsupervised activity discovery technique uses graph clustering to discover the normal structure of activity patterns in the data. Upon determination of the normal activity structure, the normal activity structure is used to detect abnormal occurrences of events.

The following first considers the problem of unsupervised detection of anomalies in activity occurrences in a time series and other types of data. The object is to locate abnormalities in frequent activities, meaning that, in contrast to previous techniques that consider any irregular subsequence as a potential anomaly, some embodiments can select or restrict the anomaly candidates to subsequences that are sufficiently similar to the normal activity structure discovered in the time series. In one embodiment, anomaly detection involves processing of a multi-dimensional time series (aka., multivariate time series), and the projection of anomalies and activities among a set of related time series. However, the techniques described herein can be applied to single-dimensional time series as well as other types of data. Also, an improved technique is applied to single-dimensional time series in order to discover perceptual primitives of activities in the time series and leverage physical attributes of data to cluster these primitives. One advantage of the current technique is that it doesn't leverage a priori information about time sequences.

1. Problem Definition

In this section, an example of anomaly in frequent activities is demonstrated using a synthetic set of time series, and the problem formulation is then presented.

1.1 Illustrative Example

Figure 1:
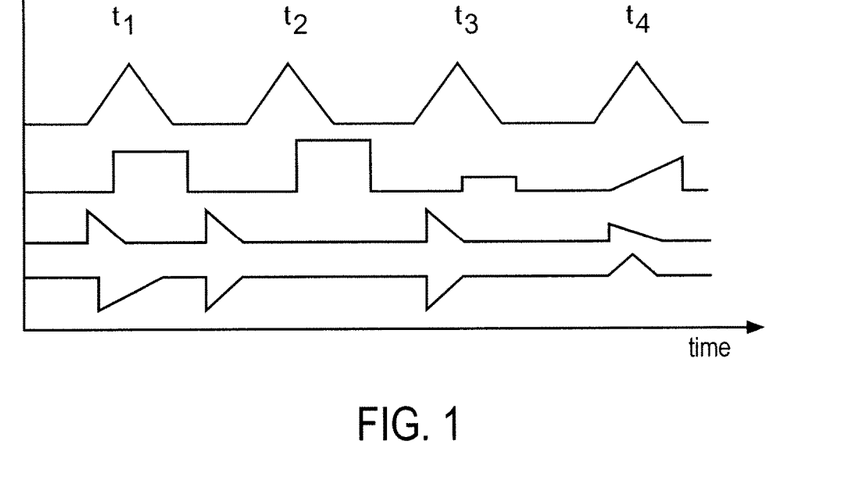
FIG. 1: A example of a time series and occurrences of an activity, according to an embodiment of the invention.

Since the notion of abnormal activity can be broad, depicted is an example in FIG. 1 to illustrate a concept of abnormal activity, according to an embodiment of the invention. Assume that time $t_1$ includes a normal occurrence of an activity that is projected in all four dimensions of the time series. Time instances $t_2$ and $t_3$ include two abnormal activity occurrences. At time $t_2$ similar patterns are projected on the time series. However, the high variation in temporal appearance of the patterns in two of the four dimensions denotes an abnormality in the activity occurrence. The activity occurrence at time $t_3$ is classified an abnormality since the rectangular pattern occurring in the second time series has a high variation comparing to the pattern in $t_1$. Finally, at time $t_4$, two of the patterns projected on the time series are different from the patterns of $t_1$, while two others have similarity. Due to the high variation of the most of the patterns at this time instance, such an occurrence may be classified as an abnormal occurrence of the same activity that occurred in $t_1$, but such occurrence may also be classified as an inherently different activity in the time series. One solution considers the application and the history of the activity occurrences in a long time series to decide on a proper classification in such a situation.

Next, a formal specification is presented for the problem of detecting abnormal activities in multi-dimensional time series, which is applicable to monitoring systems with multiple sensors.

1.2 Problem Formulation

This section sets forth certain specifications and notations used in remaining sections for some embodiments of the invention. Note that certain terms will be understood to one of ordinary skill in the art, such as time series, subsequence, Euclidean distance, and so forth, and those terms need not be further elaborated below.

Specification 2.1. Multi-dimensional time series: a multi-dimensional time series $M=\{T_1, \ldots, T_q\}$ includes q time series with equal length (n). The specification of equal length can be modified or relaxed for some embodiments.

Specification 2.2. Multi-dimensional subsequence: a multi-dimensional subsequence $S=\{s_1, \ldots, s_p\}$ includes p subsequences, where there exists at least one subsequence $s_i$, $1 \leq i \leq p$ such that $s_i$ has temporal overlap with at least another (or all other) subsequences in S.

Note that the members of S can be scattered among any subset of dimensions of a multi-dimensional time series M (e.g., $p \leq q$). In addition, the members of S can be different in the shape and length.

Specification 2.3. Activity: an activity is a multi-dimensional subsequence $A=\{a_1, \ldots, a_x\}$ with recurrent occurrences in the multi-dimensional time series. The occurrences of the activity A are noted as $A^1 \ldots A^k$, when A has k occurrences.

Specification 2.4. Abnormal Activity Occurrence: a Multi-dimensional subsequence $R=\{r_1, \ldots, r_y\}$ is an abnormal occurrence of the activity A if $$\begin{cases} \alpha < \dfrac{|R \cap A|}{|A|} < 1 \\ \text{occurences}(R) < \beta \cdot \text{occurrences}(A) \end{cases}$$

Here, A is a multi-dimensional subsequence representing an activity. |R∩A| is the total number of similar subsequences in A and R. Occurrences(S) denotes the total number of occurrences of the multi-dimensional subsequence S in a time series. $\alpha<1$ is the abnormality similarity constant or parameter associated with a particular application, and denotes the minimum similarity that should exist between the normal and abnormal occurrences of an activity. In addition, $\beta<1$ is the abnormality frequency constant or parameter, and denotes whether a multi-dimensional subsequence is an independent activity or is an abnormal occurrence of the same activity. The last two constants are input parameters for the current technique, and are discussed in later sections.

In order to detect abnormalities, it is first desired to discover a common activity occurring in the time series and to locate its occurrences. In the next section, an overall approach is presented, and main phases for unsupervised activity and abnormality detection are also presented. Each phase is described in detail in the following sections.

2. Approach

Figure 2:
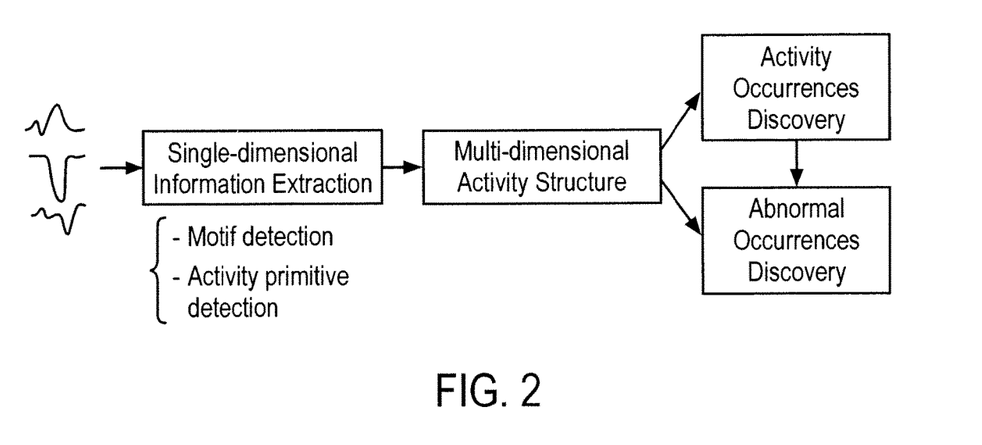
FIG. 2: An approach for activity detection and anomaly detection in multi-dimensional time series, according to an embodiment of the invention.

FIG. 2 depicts a general overview of an approach for abnormal and normal activity occurrence detection in multi-dimensional time series, according to one embodiment of the invention. In a first phase, each dimension of the time series is processed separately (serially or in parallel) to extract recurrent patterns and meaningful subsequences. These patterns are considered as primitives for activities, which are projected in more than one dimension of a set of time series. Two techniques can be implemented for this first phase: time series motif detection, and an activity primitive detection based on physical attributes of the data. In one embodiment, the activity primitive discovery technique is designed for wearable sensors. The single-dimensional activity primitives extracted in this phase can be analyzed to discover the structure of dominant multi-dimensional activities in the set of time series (phase 2). This phase uses a graph clustering approach to construct the activity structure. Thereafter, using the activity structure, all of the activity occurrences (both normal and abnormal) in the time series are extracted from the time series (phase 3). Finally, the abnormal activity occurrences are discriminated from the normal occurrences, by leveraging the information from the previous phases (phase 4).

In one embodiment, activities can include activities involving physical movement, such as walking, running, or a heartbeat as measured by an electrocardiogram (ECG). Detection of anomalies in instances of these activities can help to detect, for example, an increased risk of falls or an increased risk of a heart attack. Alternatively, activities can include activities involving varying electrical signals or other signals indicative of bodily function, such as variations in brain waves. Detection of anomalies in instances of these activities can help to detect, for example, an increased risk of seizures.

3. Unsupervised Activity and Abnormality Discovery

The following presents the use of two techniques in extracting meaningful subsequences from each dimension of a multi-dimensional time series. Motif detection in time series is a general approach to detect recurrent subsequences in a set of subsequences or in long time series. The use of motif detection is presented in the context of activity primitive extraction. While the performance of applying this technique is presented, further details are also presented for a domain specific technique for wearable motion sensors.

3.1 Frequent Patterns in Single-Dimensional Time Series

The first step in unsupervised activity discovery is to extract recurrent patterns in each dimension of the time series. Such recurrent patterns can be considered as the primitives of activities that are projected on several dimensions of a set of time series.

Motif detection is one approach for discovering recurrent patterns in time series. Time series motifs are approximately repeated subsequences in a longer time series data.

In this section, a probabilistic method is presented for motif discovery. By applying the motif detection mechanism to data collected from wearable sensors, the following shortcomings can be observed.

Figure 3:
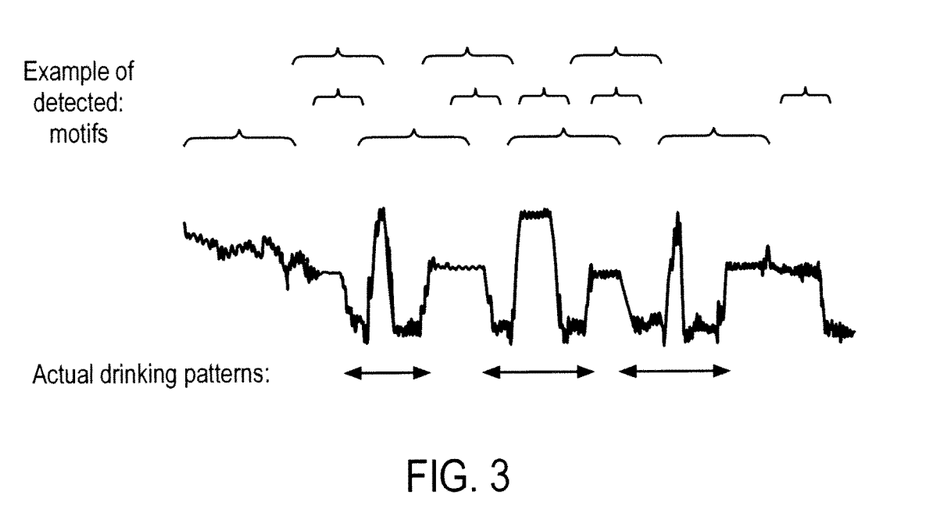
FIG. 3: The acceleration of a wrist, in three consecutive occurrences of drinking activity, according to an embodiment of the invention.

First, motif detection techniques are generally sensitive to the length of the motif subsequences and specify the candidate length of the motif as an input parameter. This typically involves a priori knowledge of the activity primitives length, which is undesirable for an unsupervised activity discovery process. In addition, human activities tend to be carried out with variation in their pace, and as a result the length and shape of activity primitives can differ for each activity occurrence. For example, FIG. 3 depicts acceleration data collected from an accelerometer worn on a wrist of a human subject while he repeated the same action of drinking water from a glass. From FIG. 3, it can be observed that occurrences of the same drinking activity can differ in length, even when performed by the same subject. Therefore, the efficiency of directly applying a motif detection technique to cluster subsequences together as one motif is decreased. Note that the effect of such variations can be reduced by using techniques such as Dynamic Time Warping. However, the variation in the length of patterns can dramatically increase the search space for motif subsequences and can decrease the efficiency and the speed of the motif detection process significantly. FIG. 3 also depicts the output of applying the motif detection technique on the time series with several subsequence lengths as input. Note how due to the sensitivity of the technique to the input motif length, different motifs are captured in each execution of the technique.

In many applications, including those with the purpose of human activity monitoring, one distinctive property of an activity is the deviation it causes in the sensor data compared to its default or stable value. For example, in the acceleration data of FIG. 3, the three drinking actions show similar minimum and maximum values in their peak and valley patterns, since the final orientation of the wrist is similar in all occurrences of the activity. An indirect approach for applying motif detection is to cluster the subsequences that show transitions between similar stable minimum and maximum values. However, changing the speed of the motion causes the slopes to vary, and, hence, the motif detection technique can fail in clustering such short subsequences efficiently (or a high number of false positives can be detected along with valid motif subsequences).

Observing the above shortcomings of applying the motif discovery technique, the following section presents an improved technique that considers the specific features of time series data in wearable sensors, such as those including motion and pressure sensors. In the next section, a domain specific technique is presented for locating activity primitives in single-dimensional time series.

3.2 Activity Primitive Discovery in Single-Dimensional Time Series

As described earlier, in many motion monitoring applications, acceleration sensors are the primary source of data. Several multi-dimensional acceleration sensors can be placed on a body in order to comprehensively monitor motion of parts of the body. Observing several applications of human motion monitoring systems, it is noticed that human motions can be projected on single dimensions of sensors as transitive patterns between two stable levels. Assuming the subsequence $a_1 \ldots a_m$ to be an activity primitive, the first and the last points in the subsequence ($a_1$ and $a_m$) are the ending point and the starting point of two stable regions (or regions with a sensor's default value) before and after the subsequence in the time series, which generally denote the situation before and after a human motion. For example, in accelerometer data, the first and the last values of an activity primitive represent the starting and final orientation of the accelerometer. Therefore, an activity primitive can be specified to be a subsequence between two consecutive stable regions (or default sensor values) in the time series. In one embodiment, a stable region of a signal corresponds to a time interval during which the value of the signal remains between (average (or mean) value of the signal −X) and (average (or mean) value of the signal +X), where X can be between from about 0.1 and about 1.0 times a standard deviation of the signal. For example, X can be a value between from about 0.3 to about 0.7 times or from about 0.4 to about 0.6 times the standard deviation of the signal, such as 0.5 times the standard deviation of the signal. Such subsequences are sometimes observed as bell shape patterns (with local minimum or maximum points) or linear slopes between two stable values, which, depending on the speed and nature of the activity, can have different length and frequency. These primitives can be classified based on the physical attributes that they represent. For example, noise free acceleration data can be converted to displacement, using the following equation on a subsequence of length m:

$$\text{displacement} = D \cdot \sum_{k=1}^{m} \sum_{i=1}^{k} |\alpha_i - \alpha_j|$$

where D is the calibration constant factor, which depends on the placement of a sensor and other parameters such as the frequency of data sampling. Methodology 1, shown in Table 1, presents a technique for extracting activity primitives as subsequences projected on single-dimensional time series.

TABLE 1

Methodology 1: Single-dimensional activity primitive extraction

```
Input: Time series T = t_1..t_n
Output: List of activity primitives along with their
    occurrences location p_occurrence(1..j), start(1..j)
i ← 1
while true do
    while t_i = default_value | t_i is stable region
    do
        increment i
    end while
    start(j) ← i
    while t_i ≠ default_value & t_i is not stable region
    do
        d ← d + Σ_{i=1}^{start(j)} t_i − t_start(j)
    end while
```

TABLE 1-continued

Methodology 1: Single-dimensional activity primitive extraction

```
        length(j) ← i − start(j)
        displacement(j) ← D · d
        d ← 0
        if i = n then
            p_occurrence(1..j) ←
                discretize(displacement(1..j), length(1..j))
            return p_occurence(1..j), start(1..j)
        end if
        j ← j + 1
    end while
```

Figure 4:
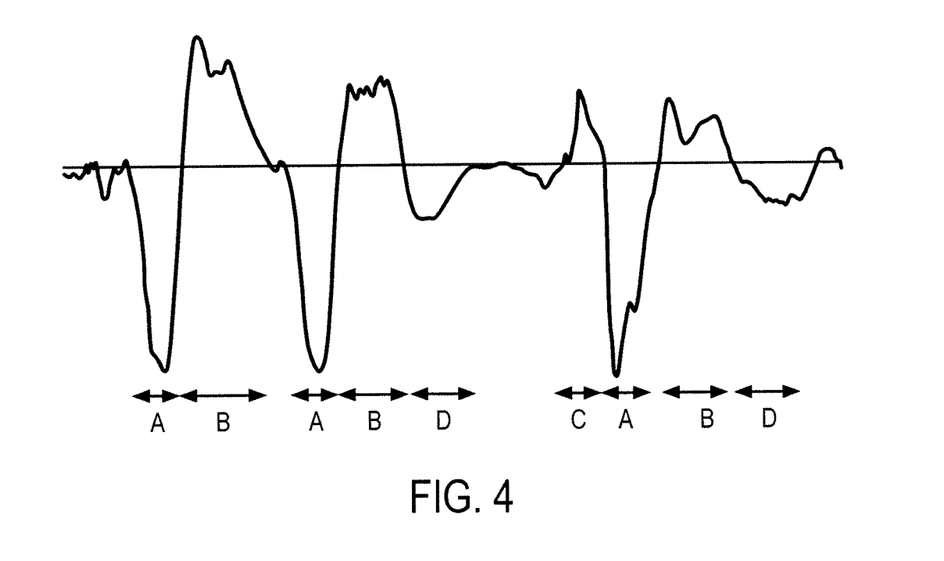
FIG. 4: The result of applying methodology 1 on a Smartcane's rotational data, according to an embodiment of the invention.

The technique extracts patterns from the time series, classifies the patterns based on the physical attribute of the data and according to a discretization cardinality, and assigns a symbol to each pattern. It also assigns a starting time to each symbol. Here, in order to discretize the calculated displacement and assign symbols, the technique considers a probability distribution of the calculated displacements and assigns symbols to primitives such that primitives are classified considering the variation of displacement during application execution. FIG. 4 depicts the result of applying this technique on a sample time series, collected from a mobility aid device incorporating a set of gyroscopic sensors (hereinafter referred to as a Smartcane).

Note that in contrast to the motif discovery technique, the improved technique leverages domain specific attributes of data (here, being the motion sensor data, which is used frequently in wearable sensors). Regardless of the technique used to discover recurrent activity patterns in single-dimensional time series, the output of this phase is passed to the multi-dimensional activity and abnormality detection phase, which is described in the next section. As noted above, other types of data, such as location data and discrete event data, can be processed. Processing of such data can yield locations and events that can be passed to the activity and abnormality detection phase.

3.3 Activity Structure in Multi-Dimensional Time Series

This section describes a technique for deriving the structure of the recurrent activities in multi-dimensional time series. Later, this technique is extended to detect abnormal activity occurrences based on the derived model for normal activities. As mentioned earlier, the first phase is to extract the activity primitives from single-dimensional time series. This phase was performed either using a general technique (e.g., motif discovery in single-dimensional time series) or via a domain specific technique described in the last section. In the second phase, the activity primitives from single-dimensional time series are clustered together, and a model for recurrent activities in multi-dimensional time series is derived.

Figure 5:
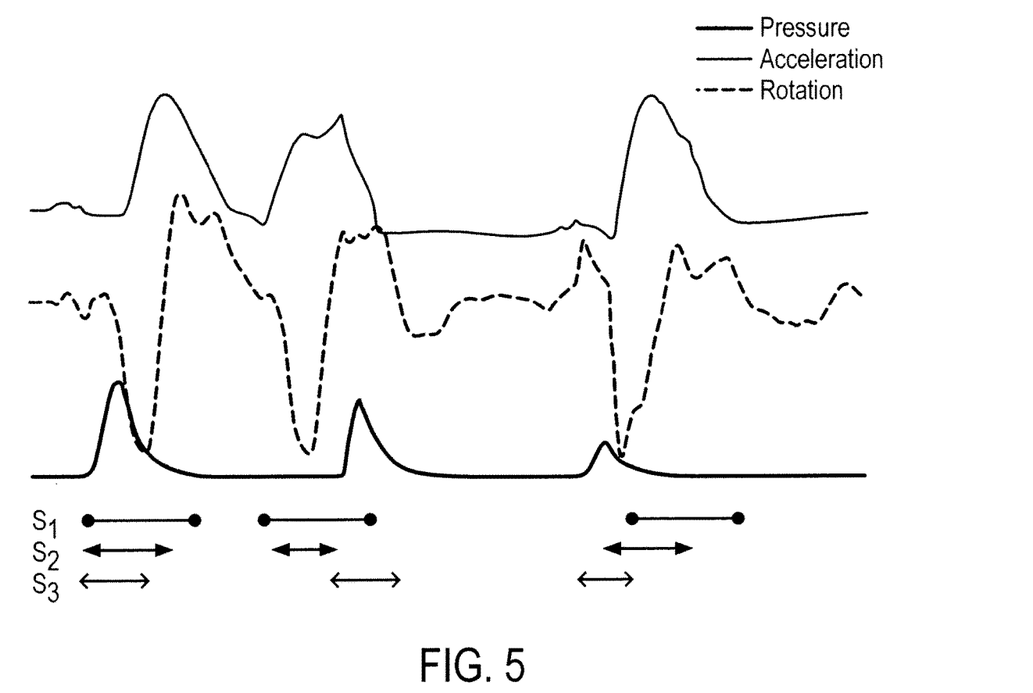
FIG. 5: Temporal variation of activity primitives in the Smartcane's usage, according to an embodiment of the invention.

As described earlier, an activity can be specified as a recurrent multi-dimensional subsequence. FIG. 5 depicts a snap-shot of data from three sensors during a walking activity using a Smartcane. The activity occurrences are projected on the three presented time series. However, while in the first occurrence of the activity in FIG. 5, $S_1$, $S_2$, and $S_3$ (primitives discovered in each dimension) are substantially synchronized or correlated in time, in the second and third occurrences, $S_2$ and $S_3$ appear with temporal variation or displacement. While in some applications, such as aerospace applications, it is desirable to capture such displacements, in wearable monitoring applications, such temporal variations can be common. Specifically, in monitoring the human motion data using acceleration and gyroscopic sensors, such variations are common, and restricting an activity specification to a set of subsequences with an exact temporal correlation or relationship can result in missing various occurrences of activities. Hence, a general notion of temporal overlap is used to specify a set of primitives as an activity structure. Statistical information from the primitive occurrences in the time series can be used to derive the structure of the most dominant activities in a multi-dimensional time series.

In order to derive multi-dimensional activity structures, a list of discovered activity primitives is converted into a weighted directed graph, so that graph clustering can be applied to derive a model of activities in multi-dimensional data. In the proposed graph, each vertex represents an activity primitive, and the weight on the vertex represents the number of occurrences of the primitive in the corresponding time series. The weight on each directed edge in the graph is calculated by the following equation:

$$e(i, j) = \frac{\text{coincidence}(i, j)}{\text{total\_occurrences}(j)}$$

Figure 6:
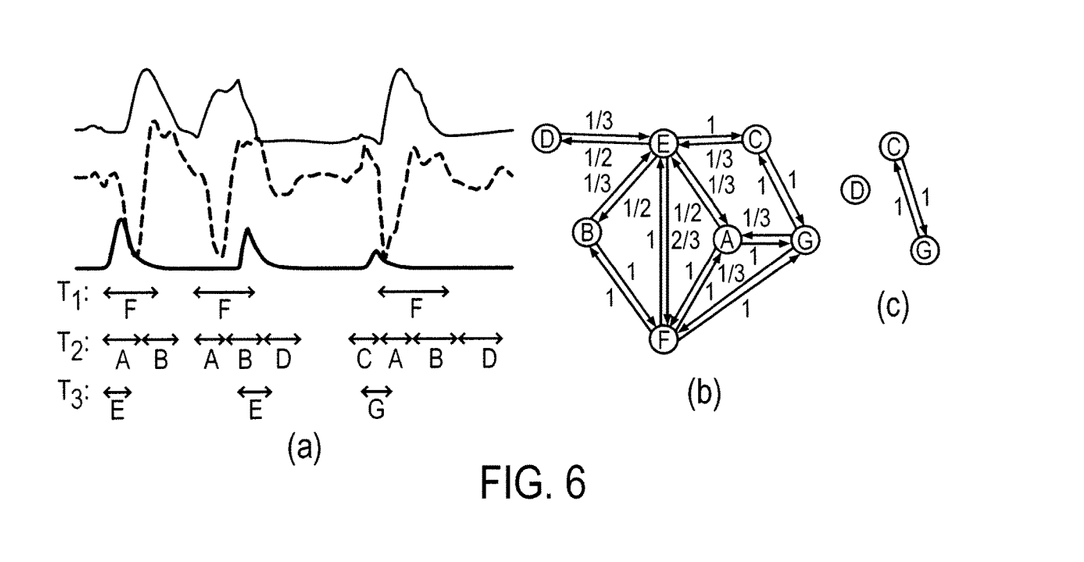
FIG. 6: (a) Three times series from the Smartcane and the detected activity primitives, (b) The resulting coincidence graph, and (c) The graph after eliminating activity primitives clustered in methodology 2, according to an embodiment of the invention.

The coincidence(i, j) denotes the number of times that there is temporal overlap between occurrences of primitives i and j. As a result, e(i, j) will be at most 1, when all the occurrences of primitive j have overlap with occurrences of primitive i, and is at least 0, when there is no overlap between occurrences of primitives i and j. FIGS. 6.*a* and 6.*b* depict an example of three time series from the Smartcane, their discovered primitives, and the resulting primitive coincidence graph.

In the next phase, a graph clustering technique is used to derive a multi-dimensional activity structure from the primitive coincidence graph. Note that according to the specification presented in Section 1.2, several activity structures can be discovered in a time series. In this embodiment, the focus is on activity structures with the highest number of occurrences in the time series and abnormal occurrences with respect to those activity structures. In addition, according to the specification, eliminating a primitive from a set of primitives that resembles an activity can still result in an activity model that is a subset of the original activity model. Here, the focus is on extracting maximal sets representing activities, where a maximal activity model is a multi-dimensional subsequence defined such that adding a primitive to it doesn't yield another activity model with multiple occurrences in the time series. Methodology 2, shown in Table 2, presents a technique for deriving the activity structures from the coincidence graph. Clustering the primitives starts with sorting the list of vertices based on the number of occurrences of the primitives. Then, the most frequent primitive is selected as a candidate core for the activity structure, and the graph is searched for primitives with high temporal correlation (e.g., temporal overlap) with the candidate core primitive. If there are several primitives with equal frequency, the one with the larger number of highly correlated neighbors is selected as the core primitive. The threshold for the correlation is set to $1-\beta$, where $\beta$ is the abnormality frequency constant. Upon construction of an activity by clustering correlated primitives, selected primitives are removed from the graph, and the technique continues for discovering new activity structures by selecting a new core activity primitive.

TABLE 2

Methodology 2: Activity structure derivation from the primitives coincidence graph

| | |
|---|---|
| 1: | Input: G(V, E) the primitives coincidence graph, total_occurrence(v) for all vertices and e($v_1$, $v_2$) for all directed edges |
| 2: | Output: S = {$S_i$} The set of most recurrent activity structures in the time series, (each $S_i$ is an activity) |
| 3: | Sort the vertices list in G in descending order of total_occurrence {if some primitives have equal frequency, then the primitive with the highest number of highly correlated neighbors has the highest priority} |
| 4: | for each vertex $v_k$ in the sorted list of vertices do |
| 5: |    Add $v_k$ to activity $S_i$ |
| 6: |    for all neighbors of $v_k$, if $e_{(j,k)} > 1 - \beta$ do |
| 7: |       Add $v_j$ to activity $S_i$ |
| 8: |       remove $v_j$ from the graph |
| 9: |    end for |
| 10: |    i ← i + 1 |
| 11: |    Update the sorted list of vertices |
| 12: | end for |
| 13: | return S = {$S_1$,...,$S_{i-1}$} |

FIG. 6.*c* depicts the results of applying the technique to the coincidence graph of the previous example shown in FIG. 6.*b*, when β is set to 0.4. As denoted in FIG. 6, a first activity structure derived includes primitives A, B, F, and E (F is the activity core primitive, due to its high number of occurrences). In one embodiment and for some applications, β can have a value from about 0.2 to about 0.8, such as from about 0.3 to about 0.7, from about 0.4 to about 0.65, from about 0.55 to about 0.65, and such as about 0.6. Upon eliminating these primitives from the graph, primitives C and G show high temporal correlation, and can be classified as a second activity structure. Note that the effective derivation of activity structures can depend on the frequency of primitives, and in some applications the frequency and coincidences are significantly higher. For example and for some applications, β can be set to less than or equal to about 0.2 or less than or equal to about 0.1, such as $0<\beta \leq 0.2$ or $0<\beta \leq 0.1$. The depicted graph is formed from a set of short time series and is selected to be relatively short to better illustrate the logic behind the technique. The graph clustering technique explained above also can be used to derive an activity structure from locations, events, primitives, or combinations thereof.

3.4 Abnormality Discovery in Activities.

In some embodiments, an anomaly (or an abnormality) can be specified as a multi-dimensional subsequence that has at least one missing primitive compared to occurrences of activity A, but which has no more than $(1-\alpha) \cdot |A|$ missing primitives, where |A| denotes a total number of primitives of activity A. In one embodiment, for some motion sensing applications, α can have a value from about 0.7 to about 0.95 or from about 0.8 to about 0.95, such as about 0.9. Methodology 3, shown in Table 3, presents a technique for detecting such multi-dimensional subsequences. The input to the technique is the list of all discovered single-dimensional activity primitives in the time series, in addition to the discovered multi-dimensional activity structure. The technique first removes primitive occurrences that are not in the activity structure from the list of primitives (lines 3-7). By scanning the remaining primitives in the list, the technique removes primitive occurrences that correspond to normal activity occurrences from the list (lines 9-14). Finally, another scanning is performed on the list of primitive occurrences, and any multi-dimensional subsequence with an abnormal activity occurrence characteristic of specification 2.4 described above is returned as the output (lines 15-23).

TABLE 3

Methodology 3: Abnormal activity occurrence discovery

1: Input: Activity structure S = {$s_1$, ..., $s_m$} and list of single-dimensional primitives p_occurrences(1 ... j) and their locations start_time(1 ... j)
2: Output: Set of abnormal activity occurrences Abnormal = {$abnormal_1$, ..., $abnormal_k$})
3:   for all primitive in p_occurrence do
4:     if primitive $\notin$ S then
5:       Remove primitive from $p_o$ccurrences
6:     end if
7:   end for
8:   Sort p_occurrences based on start_time
9:   for all primitive in sorted array p_occurrences do
10:     temp_set = {all the primitive occurrences which have temporal overlap with primitive}
11:     if $\frac{|\text{temp\_set} \cap S|}{|S|} = 1$ then
12:       Remove temp_set members from p_occurrences
13:     end if
14:   end for
15:   for all Remained primitive in p_occurrences do
16:     temp_set = {all the primitive occurrences which have temporal overlap with primitive}
17:     if $\frac{|\text{temp\_set} \cap S|}{|S|} > \alpha$ then
18:       $abnormal_i$ = temp_set
19:       Remove temp_set members from p_occurrences
20:       Increment i
21:     end if
22:   end for
23:   return Abnormal = {$abnormal_j$, ..., $abnormal_i$}

Figure 7:
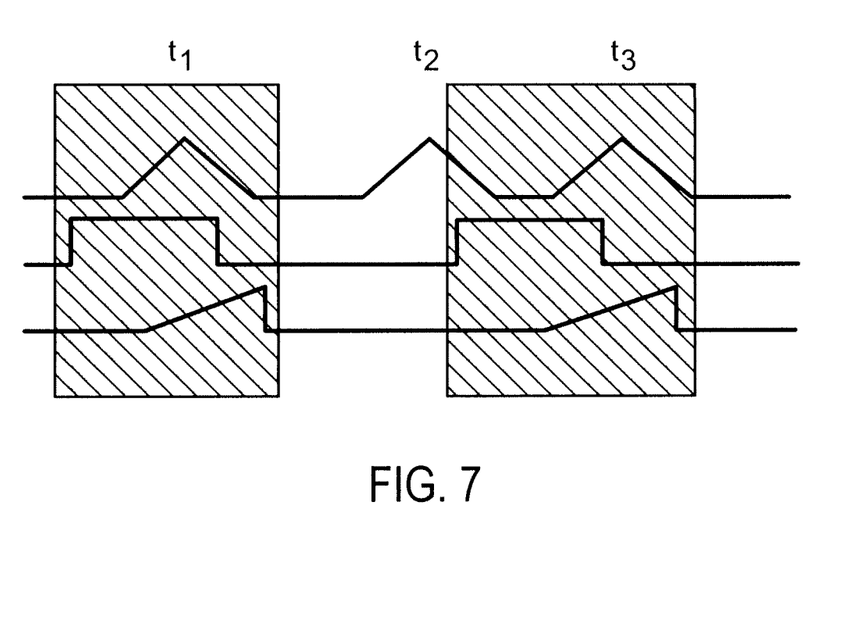
FIG. 7: The primitive at $t_2$ may be detected as an anomaly if an activity occurrence at $t_3$ is not eliminated, according to an embodiment of the invention.

The reason for the two consecutive scanning iterations of the primitive occurrences list is illustrated in FIG. 7. A primitive occurrence can yield more than one multi-dimensional subsequence, with only a subset (e.g. one) of them being an activity occurrence. Hence, in the first iteration, all of the activity occurrences are discovered, and their corresponding primitives are removed from the primitives list, in order to avoid false positives in detecting abnormal occurrences. In the example of FIG. 7, while in the first iteration the patterns in $t_2$ are candidates for abnormality, by eliminating the patterns of activity occurrence at time $t_3$, the similarity of patterns in $t_2$ to the activity patterns (which occurred in $t_1$) becomes less than $\alpha$, and, hence, the patterns in $t_2$ are not classified as an abnormal occurrence of the activity.

Once activities and anomalies in activities are detected, some embodiments can generate an alert, a report, a log, or other indication of such activities and anomalies, whether in visual form, audio form, tactile form, or a combination thereof. In one embodiment, activities can include activities involving physical movement, such as walking, running, or a heartbeat as measured by an ECG. Detection of anomalies in instances of these activities can lead to the generation of an alert or other indication of an increased risk of falls or an increased risk of a heart attack. In another embodiment, activities can include activities involving varying electrical signals or other signals indicative of bodily function, such as variations in brain waves. Detection of anomalies in instances of these activities can lead to the generation of an alert or other indication of an increased risk of seizures.

Figure 8:
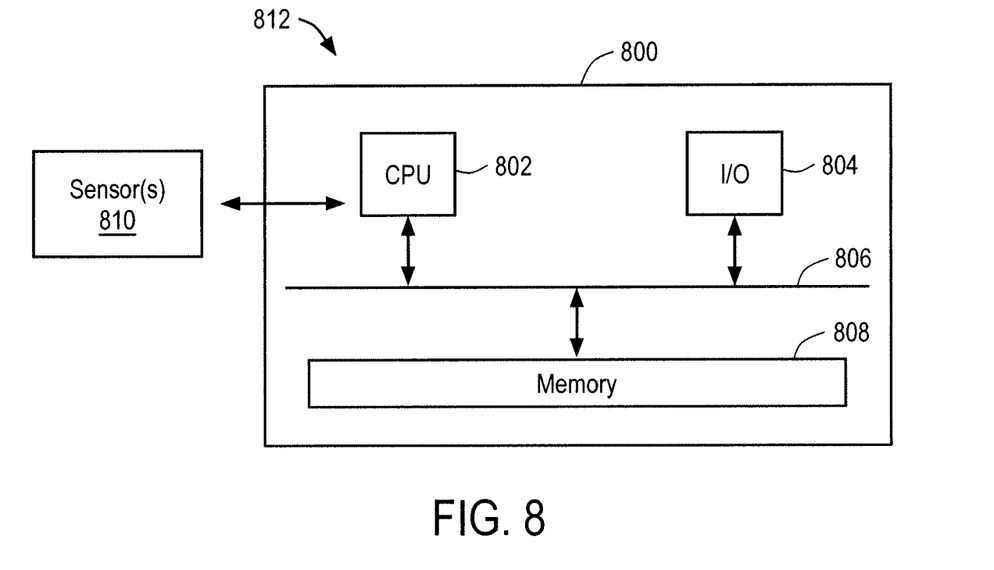
FIG. 8: A system configured in accordance with an embodiment of the invention.

FIG. 8 illustrates a system 812 configured in accordance with one embodiment of the present invention. The system 812 includes a computer 800, which includes a central processing unit (CPU) 802 connected to a bus 806. Input/output (I/O) devices 804 are also connected to the bus 806, and can include a keyboard, mouse, display, and the like. An executable program including a set of modules for discovering activities and abnormalities in time series data as described above is stored in memory 808, which is also connected to the bus 806. For example, the memory 808 can store an activity primitive extraction module to execute methodology 1, an activity structure derivation module to execute methodology 2, and an abnormal activity occurrence discovery module to execute methodology 3. The memory 808 can also store an alert module to generate alerts or other indications of anomalies in bodily movement or bodily functions. As shown in FIG. 8, the system 812 also includes a set of sensors 810, which is connected to the computer 800 via a wired or wireless link, and from which time series data can be collected for processing by the computer 800. Although the sensors 810 are shown separate from the computer 800, these components can also be combined in other embodiments, such as within a sensing device.

An embodiment of the invention relates to a non-transitory computer-readable storage medium having computer code thereon for performing various computer-implemented operations. The term "computer-readable storage medium" is used herein to include any medium that is capable of storing or encoding a sequence of instructions or computer codes for performing the operations, methodologies, and techniques described herein. The media and computer code may be those specially designed and constructed for the purposes of the invention, or they may be of the kind well known and available to those having skill in the computer software arts. Examples of computer-readable storage media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits ("ASICs"), programmable logic devices ("PLDs"), and ROM and RAM devices. Examples of computer code include machine code, such as produced by a compiler, and files containing higher-level code that are executed by a computer using an interpreter or a compiler. For example, an embodiment of the invention may be implemented using Java, C++, or other object-oriented programming language and development tools. Additional examples of computer code include encrypted code and compressed code. Moreover, an embodiment of the invention may be downloaded as a computer program product, which may be transferred from a remote computer (e.g., a server computer) to a requesting computer (e.g., a client computer or a different server computer) via a transmission channel. Another embodiment of the invention may be implemented in hardwired circuitry in place of, or in combination with, machine-executable software instructions.

While the invention has been described with reference to the specific embodiments thereof, it should be understood by those skilled in the art that various changes may be made and equivalents may be substituted without departing from the true spirit and scope of the invention as defined by the appended claims. In addition, many modifications may be made to adapt a particular situation, material, composition of matter, method, operation or operations, to the objective, spirit and scope of the invention. All such modifications are intended to be within the scope of the claims appended hereto. In particular, while certain methods may have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations is not a limitation of the invention.

What is claimed is:

1. A non-transitory computer-readable storage medium, comprising executable instructions to:
   receive time series sensor data from at least one body-worn sensor of a wearable device, the time series sensor data corresponding to measurements of a bodily activity occurring during a time interval;
   determine from the time series sensor data in the time interval at least one stable sensor value;
   identify stable regions in the time interval, each stable region corresponding to a portion of the time interval in which values of the time series sensor data remain within a predefined variation range around one of the at least one stable sensor value, the predefined variation range associated with a sensor type;
   identify subsequences in the time series sensor data, each subsequence comprising a pattern of the time series sensor data between two sequential stable regions;
   identify at least two activity primitives from the subsequences, each activity primitive representing a recurrent pattern of the time series sensor data;
   derive an activity structure relating a first subset of the at least two activity primitives, the activity structure representing a normal instance of the bodily activity;
   based on the activity structure, classify a second subset of the at least two activity primitives as an abnormal instance of the bodily activity; and
   generate, by the wearable device, a signal to an output component of the wearable device for an audible or tactile alert in response to identifying that the abnormal instance of the bodily activity has occurred.

2. The non-transitory computer-readable storage medium of claim 1, wherein the executable instructions to receive the time series sensor data include executable instructions to:
   receive a multi-dimensional time series corresponding to the measurements of the bodily activity collected from multiple sensors, and
   wherein each of the at least two activity primitives represents a single-dimensional recurrent pattern in the multi-dimensional time series.

3. The non-transitory computer-readable storage medium of claim 1, wherein the at least one stable sensor value comprises a speed value or an acceleration value.

4. The non-transitory computer-readable storage medium of claim 1, wherein the executable instructions to derive the activity structure include executable instructions to:
   classify the first subset as a normal instance of the bodily activity if the first subset has at least a minimum degree of temporal overlap.

5. The non-transitory computer-readable storage medium of claim 1, wherein the executable instructions to classify the second subset include executable instructions to:
   compare the second subset to the first subset; and
   classify the second subset as the abnormal instance of the bodily activity if the second subset omits at least one of the activity primitives included in the first subset.

6. The non-transitory computer-readable storage medium of claim 5, wherein the executable instructions to classify the second subset further include executable instructions to:
   classify the second subset as the abnormal instance of the bodily activity if the second subset includes at least a minimum number of activity primitives included in the first subset.

7. The non-transitory computer-readable storage medium of claim 1, wherein the time series sensor data correspond to measurements of a bodily movement, and further comprising executable instructions to:
   generate the alert of the abnormal instance of the bodily movement.

8. The non-transitory computer-readable storage medium of claim 1, wherein the time series sensor data correspond to measurements of a bodily function, and further comprising executable instructions to:
   generate the alert of the abnormal instance of the bodily function.

9. A non-transitory computer-readable storage medium, comprising executable instructions to configure a processor to monitor activities of a subject by monitoring data from a plurality of sensors of a wearable device, the executable instructions including instructions to:
   receive time series data corresponding to sensor measurements of the plurality of sensors of the wearable device, the time series data including components in a plurality of dimensions;
   determine a plurality of subsequences associated with the time series data, wherein each of the plurality of subsequences represents a pattern projected along one of the plurality of dimensions, the pattern being between two sequential stable regions along the one of the plurality of dimensions;
   identify a first subset of the plurality of subsequences as representing a normal instance of a first bodily activity based on a degree of temporal overlap of members of the first subset;
   identify a second subset of the plurality of subsequences as an abnormal instance of the first bodily activity, wherein identifying the second subset comprises comparing the second subset to the first subset, and classifying the second subset as the abnormal instance of the first bodily activity that comprises determining that the second subset omits at least one subsequence included in the first subset and determining that the second subset includes at least a minimum number of subsequences included in the first subset; and
   generate, by the wearable device, an indication of the abnormal instance of the first bodily activity, to direct an output component of the wearable device to generate an audible or tactile alert.

10. The non-transitory computer-readable storage medium of claim 9, wherein the two stable regions are two of a plurality of stable regions, and each of the plurality of stable regions is a portion of the time series data in which a value of the time series data is within one of a plurality of predefined variation ranges.

11. The non-transitory computer-readable storage medium of claim 9, wherein the executable instructions to identify the first subset include executable instructions to:
   perform graph clustering on vertices corresponding to the plurality of subsequences.

12. The non-transitory computer-readable storage medium of claim 11, wherein the executable instructions to perform graph clustering include executable instructions to:
   assign weights to the vertices based on a degree of temporal overlap of respective pairs of the vertices.

13. The non-transitory computer-readable storage medium of claim 9, further comprising:

identify a third subset of the plurality of subsequences as a normal instance of a second bodily activity based on a degree of temporal overlap of members of the third subset, wherein the first bodily activity is distinct from the second bodily activity.

14. The non-transitory computer-readable storage medium of claim 13, further comprising:
   identify a fourth subset of the plurality of subsequences as an abnormal instance of the second bodily activity based on comparing the fourth subset to the third subset; and
   produce an indication of the abnormal instance of the second bodily activity.

15. A system for abnormality detection, comprising:
   a processing unit; and
   a memory connected to the processing unit and including executable instructions to configure the processing unit to:
   receive time series data from a plurality of body-worn sensors of a wearable device, the time series data of the plurality of body-worn sensors together forming a multi-dimensional time series, the multi-dimensional time series corresponding to measurements of a bodily activity;
   determine for each dimension of the multi-dimensional time series a plurality of primitives, each primitive occurring between two stable regions in each of the dimensions;
   determine a plurality of multi-dimensional subsequences comprising the primitives from each dimension of the multi-dimensional time series, the plurality of multi-dimensional subsequences including patterns of the time series data of each of the dimensions;
   identify a first multi-dimensional subsequence of the plurality of multi-dimensional subsequences, including a first plurality of primitives presenting a recurrent pattern of the time series data of a first dimension of the first multi-dimensional subsequence, as a normal instance of the bodily activity;
   identify a second multi-dimensional subsequence of the plurality of multi-dimensional subsequences, including a second plurality of primitives presenting a recurrent pattern of the time series data of a second dimension of the second multi-dimensional subsequence, as an abnormal instance of the bodily activity based on a degree of similarity between members of the second multi-dimensional subsequence and members of the first multi-dimensional subsequence; and
   generate, by the wearable device, a signal to an output component of the wearable device for an audible or tactile alert in response to identifying that the abnormal instance of the bodily activity has occurred.

16. The system of claim 15, wherein the executable instructions to identify the second multi-dimensional subsequence include executable instructions to:
   classify the second multi-dimensional subsequence as the abnormal instance of the bodily activity if the second multi-dimensional subsequence omits at least one member included in the first multi-dimensional subsequence, and if the second multi-dimensional subsequence includes at least a minimum number of members included in the first multi-dimensional subsequence.

17. The system of claim 15, where each stable region is defined as a time series region in which data in the region falls within a variation range, the variation range being predefined for a sensor corresponding to the dimension.

18. A non-transitory computer-readable storage medium, comprising executable instructions to:
   receive discrete event data about one or more events occurring during a time interval;
   determine a plurality of patterns associated with sensor data received from at least one body-worn sensor of a wearable device during the time interval, wherein each of the plurality of patterns represents a characteristic pattern in a portion of the time interval;
   derive an activity structure from a first subset, the first subset comprising at least one first event member of the one or more events and at least one first pattern member of the plurality of patterns, the first event members being correlated in time with corresponding first pattern members;
   based on the activity structure, classify a second subset as an abnormal instance, the second subset comprising at least one second event member of the one or more events and at least one second pattern member of the plurality of patterns, the second event members being correlated in time with second corresponding pattern members, wherein classifying the second subset comprises comparing the second subset to the first subset, and classifying the second subset as the abnormal instance of the first bodily activity comprises determining that the second subset omits at least one subsequence included in the first subset and determining that the second subset includes at least a minimum number of subsequences included in the first subset; and
   generate, by the wearable device, a signal to an output component of the wearable device for an audible or tactile alert in response to identifying that the abnormal instance has occurred.

19. A non-transitory computer-readable storage medium, comprising executable instructions to:
   receive a combination of multi-dimensional time series data and discrete event data about a bodily activity occurring during a time interval, the multi-dimensional time series data received from a plurality of body-worn sensors of a wearable device;
   determine a plurality of primitives and events associated with the time series data and the event data, wherein each of the plurality of primitives represents a characteristic pattern in a portion of the time interval;
   derive an activity structure relating a first subset of the plurality of primitives and events that are correlated in time;
   based on the activity structure, classify a second subset of the plurality of primitives and events as an abnormal instance of the bodily activity, wherein classifying the second subset comprises comparing the second subset to the first subset, and classifying the second subset as the abnormal instance of the bodily activity comprises determining that the second subset omits at least one subsequence included in the first subset and determining that the second subset includes at least a minimum number of subsequences included in the first subset; and
   generate, by the wearable device, a signal to an output component of the wearable device for an audible or tactile alert in response to identifying that the abnormal instance of the bodily activity has occurred.

20. A non-transitory computer-readable storage medium, comprising executable instructions to:
   receive a combination of location data, multi-dimensional time series data, and discrete event data about a bodily activity occurring during a time interval, the multi-dimensional time series data being received from a plurality of body-worn sensors of a wearable device;

determine a plurality of locations, primitives, and events associated with the location data, multi-dimensional time series data, and discrete event data, wherein each of the plurality of locations, primitives, and events represents a characteristic pattern in a portion of the time interval;

derive an activity structure relating a first subset of the plurality of locations, primitives, and events that are correlated in time;

based on the activity structure, classify a second subset of the plurality of locations, primitives, and events as an abnormal instance of the bodily activity, wherein classifying the second subset comprises comparing the second subset to the first subset, and classifying the second subset as the abnormal instance of the bodily activity comprises determining that the second subset omits at least one subsequence included in the first subset and determining that the second subset includes at least a minimum number of subsequences included in the first subset; and generate, by the wearable device, a signal to an output component of the wearable device for an audible or tactile alert in response to identifying that the abnormal instance of the bodily activity has occurred.

* * * * *